United States Patent [19]
Mannucci

[11] 3,975,103
[45] Aug. 17, 1976

[54] PHOTOMETRIC LIQUID ANALYZERS FOR USE IN CLINICAL OR CHEMICAL LABORATORY ANALYSIS

[75] Inventor: Enzo Sergio Mannucci, Siena, Italy

[73] Assignee: Istituto Sieroterapico A Vaccinogeno Toscano "Sciavo" S.p.A., Siena, Italy

[22] Filed: May 14, 1975

[21] Appl. No.: 577,786

[30] Foreign Application Priority Data

May 17, 1974 Italy .................................. 11603

[52] U.S. Cl. .............................. 356/184; 250/564; 250/573; 356/188; 356/189
[51] Int. Cl.² .......................................... G01J 3/46
[58] Field of Search ........... 356/180, 181, 184, 188, 356/189; 250/564, 573

[56] References Cited
UNITED STATES PATENTS

3,706,499  12/1972  Rapoza et al. ...................... 356/184
3,811,780  5/1974  Liston .................................. 356/180

Primary Examiner—Vincent P. McGraw
Attorney, Agent, or Firm—Haseltine, Lake & Waters

[57] ABSTRACT

A photometric liquid analyzer for use in clinical or chemical laboratory analysis comprises a lower housing containing a photometric unit. A liquid sample to be analyzed is introduced into a container of the photometric unit and light is then passed through the container and sample and the degree of light absorption is measured using a photomultiplier and associated electronic circuitry. An upper housing of the analyzer is inclined forwardly and upwardly with respect to the lower housing and contains a print-out unit for printing out the photometric analysis results.

7 Claims, 8 Drawing Figures

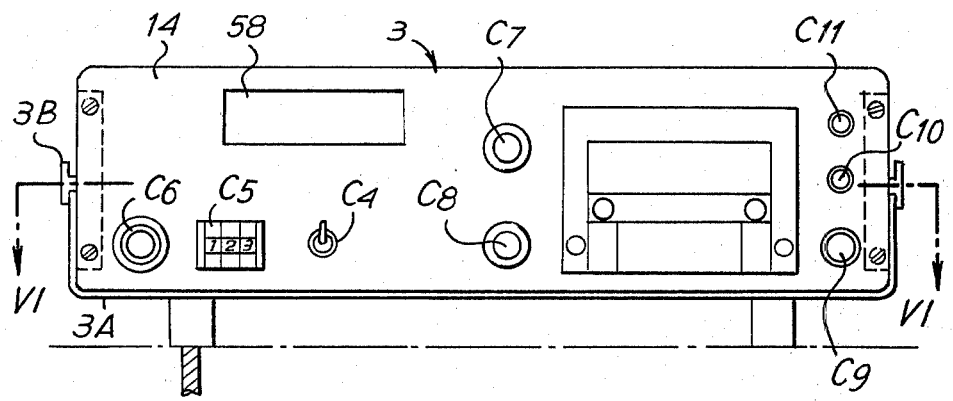
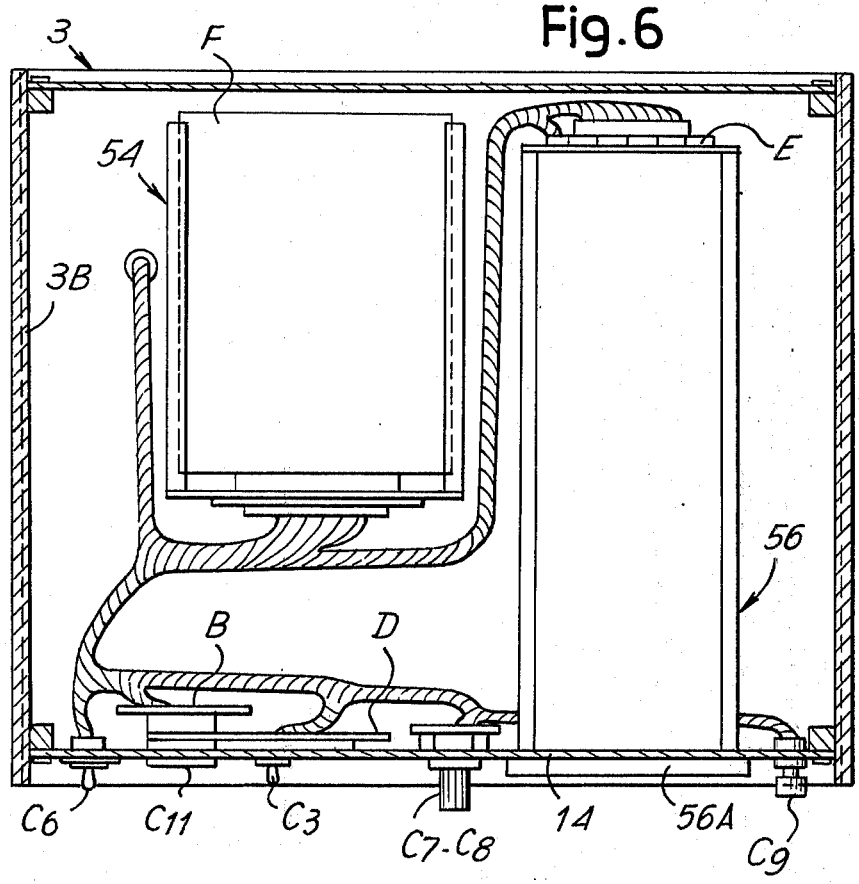

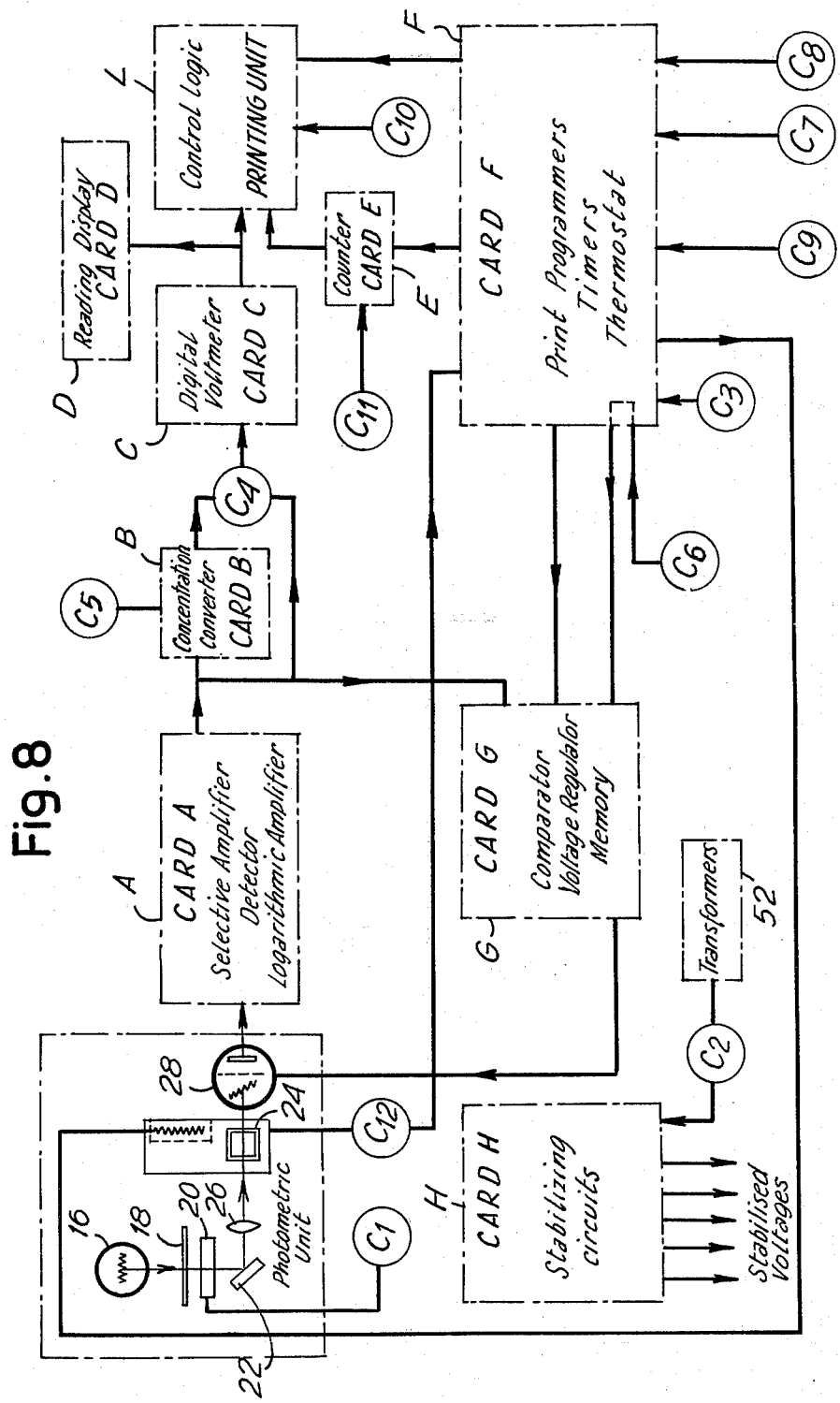

PHOTOMETRIC LIQUID ANALYZERS FOR USE IN CLINICAL OR CHEMICAL LABORATORY ANALYSIS

BACKGROUND OF THE INVENTION

This invention relates to photometric liquid analysers, for example for use in clinical or chemical laboratory analyses.

SUMMARY OF THE INVENTION

According to the invention there is provided a photometric liquid analyser, comprising: a photometric unit having a light source, a rotary modulator arranged to modulate light from the light source, at least one interferential filter through which the modulated light is arranged to pass, a photomultiplier, an optical system arranged to focus the said light, after passage through the filter, onto the photomultiplier, and a liquid-sample container unit movable into and out of an analysis position; the liquid-sample container unit comprising a container lying in the path of light passing from the optical system to the photomultiplier when the container unit is in the analysis position, a cycle-start automatic control arranged to initiate analysis of a liquid sample in the container upon return of the container unit into the analysis position, a suction-emptying system for removing analysed liquid from the container, and a thermostatic control system for regulating the temperature of liquid in the container; electronic circuit means connected to the output of the photomultiplier to receive and process signals fed therefrom caused by light which has passed through the liquid sample in the container; and a print-out unit connected to the circuit means to receive the processed signals and to print out analysis readings in dependence thereon.

BRIEF DESCRIPTION OF THE DRAWINGS

A photometric liquid analyser embodying the invention will now be described, by way of example, with reference to the accompanying diagrammatic drawings, in which:

FIG. 5 is a front elevation of an upper housing of the analyser with a lid of the housing removed;

FIG. 6 is a section on line VI—VI of FIGS. 1 and 5;

FIG. 8 is a block diagram of the various functional elements of the analyser.

DESCRIPTION OF THE PREFERRED EMBODIMENT

Figure 1:
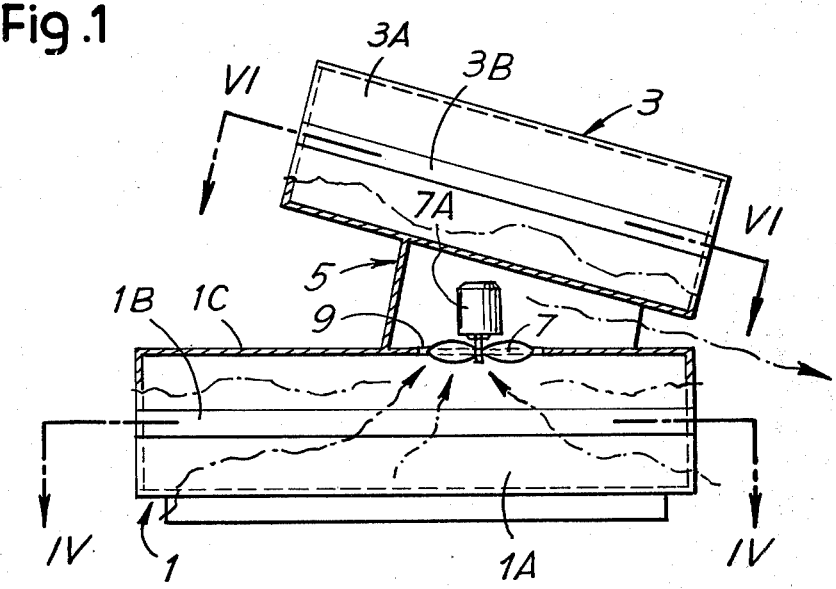
FIG. 1 is a side elevation, partly in section, of the analyser showing a cooling system of the analyser.
Figure 2:
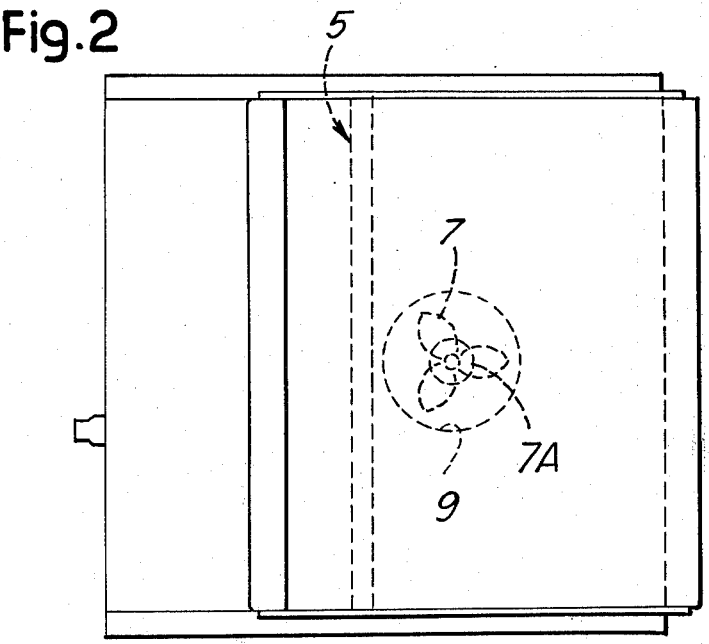
FIG. 2 is a plan view of the analyser illustrating part of the cooling system.
Figure 4:
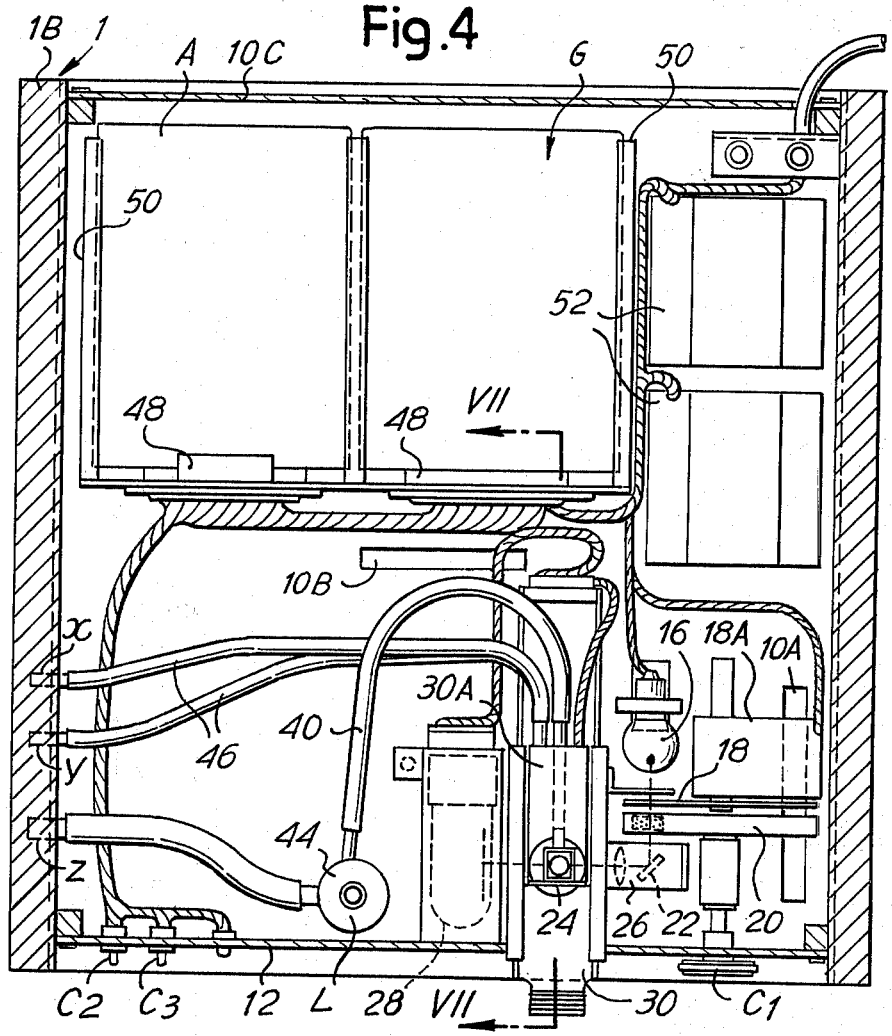
FIG. 4 is a section on line IV—IV of FIGS. 1 and 3.

As shown in FIG. 1, the analyser has a lower housing 1, as well as an upper housing 3 which is inclined upwardly and forwardly. The lower housing 1 contains a photometric unit including a liquid-sample container unit, and electronic circuit boards, and the upper housing 2 contains a print-out unit and further electronic circuit boards. Between the upper and lower housings is an intermediate housing 5 open at its rear. The housing 5 contains a motor 7A drivingly coupled to a fan 7 which is disposed within an opening 9 in the lid 1C of the lower housing 1. The fan 7 is a low speed, high throughput fan and sucks air from the interior of the housing 1 which has air intake openings 10A, 10B and 10C, (FIG. 4) so located as to facilitate a cooling air flow through the housing. The intake 10C is covered with a grid forming part of the back of the housing 1. Air sucked by the fan 7 through the opening 9 is blown out of the open rear of the intermediate housing 5.

Figure 3:
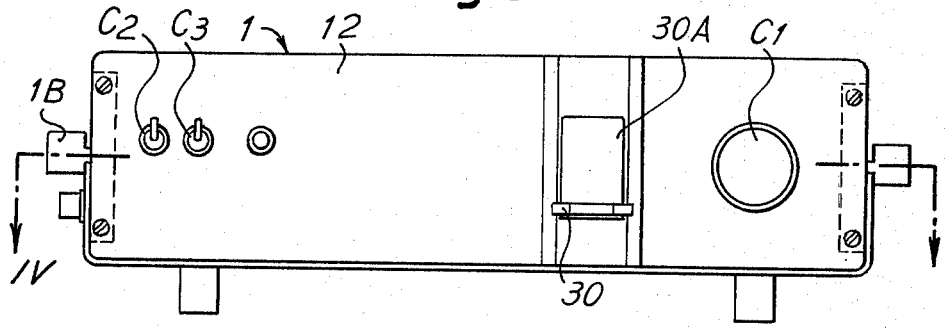
FIG. 3 is a front elevation of a lower housing of the analyser with a lid of the housing removed.

The two housings 1 and 3 are similar in structure, each having a lower shell 1A and 3A, respectively, joined by matching rules in the form of metal strips 1B and 3B respectively to lids 1C and 3C respectively. The housing 1 and 3 also have front panels 12 and 14 (FIGS. 3 and 5) respectively.

The photometric unit comprises a tungsten filament lamp 16 (for example a 15 watt lamp) and a rotary modulator 18 arranged to intermittently interrupt the light from the lamp 16 and thereby provide a modulated light source (for example modulated at 1000 Hertz) independently of and unaffected by external light sources. The modulator 18 is driven by a motor 18A which is cooled by air flowing through the intake 10A. Interferential light filters (for example of the narrow band Balzers type) are arranged on a drum 20 which may, for example, carry 12 such filters and which is rotatable by a control C1 to select a desired filter. Light passing through the selected filter is reflected through 90° by a mirror 22 and is then focused onto a photomultiplier 28, by means of an optical system represented by a lens 26. A liquid-sample container 24 is arranged in the path of light passing through the lens 26 to the photomultiplier 28. The photomultiplier is of the type with ultra-violet spectral sensitivity.

The liquid-sample container unit (FIGS. 4 and 7) comprises a slide member 30 carrying a body 30A in which the container 24 and a funnel 24A are arranged. In the bottom surface of the slide member 30 are two positioning grooves 32 and 34 which co-operate with a tappet roller 36B to define respectively an inner position of the liquid-sample container unit in which the container 24 is aligned between the lens 26 and the photomultiplier 28, and an outer position of the unit in which a liquid sample to be analysed can be introduced into the container 24 through the funnel 24A. The roller 36B is mounted on a lever 36 adjacent one end thereof. The lever 36 is pivoted at 36A and is arranged to actuate an automatic zero-setting microswitch 38. The roller 36B is resiliently urged into cooperation with the two grooves 32 and 34 both to define the inner and outer positions of the unit and to cause actuation of the microswitch 38 when the slide member 30 is in its outer position in which the roller 36B engages the groove 34; this actuation results from the groove 34 (which is deeper than the groove 32) allowing the lever 36 to rotate slightly in a clockwise direction to move the lever 36 to operate the microswitch 38.

A discharge tube 40 for the container 24 is fixed to a terminal fitting of a conduit 42 which is formed in the container walls and communicates with the interior of the container through the bottom thereof to enable liquid to be sucked from the container. The tube 40 is flexible and is connected to a valve 44 (see FIG. 4) which selectively connects and disconnects the tube 40 from a suction source and a drain conduit for analysed liquids. Tubes 46 supply and remove a thermostaticacting liquid from a liquid circuit 48 within the body 30A to stabilize the temperature of the body 30A (and therefore of the liquid under analysis in the container 24) in cooperation with a heating means controlled by a thermostat.

Figure 7:
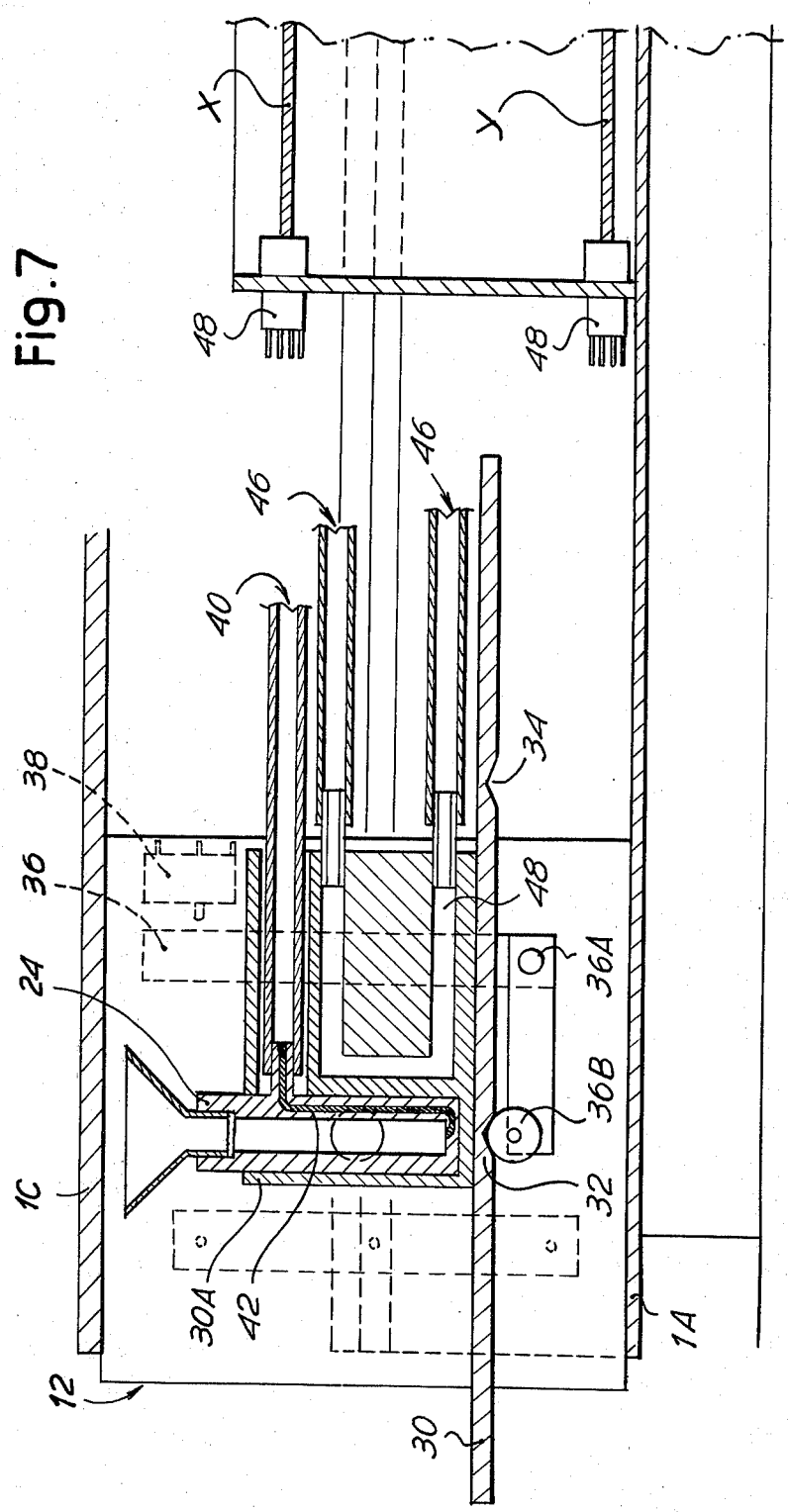
FIG. 7 is a section to an enlarged scale on line VII—VII of FIG. 4.

Connectors 48 (FIGS. 4 and 7) effect electrical connections with the electronic circuit boards located in the lower housing in rearwardly accessible seats 50 and electrical leads from the connectors 48 pass into the upper housing for connection with circuit boards located therein. In FIG. 7, upper and lower circuit boards X and Y are shown to indicate the position and relative size of the boards in the lower housing 1. Circuit boards A, H, G, to be described hereinafter, are located in the lower housing 1 which also accommodates power supply transformers 52.

The upper housing 3 has a seat 54 for electronic circuit boards C and F, and circuit boards B and D are located on the front panel 14. The print-out unit 56 has a front section 56A which, as shown in FIGS. 5 and 6, forms part of the panel 14.

The electronic circuitry of the analyser which is contained on the circuit boards, will now be described with reference to FIG. 8.

The circuit board A has a frequency-selective amplifier, a detector, and a logarithmic (or anit-logarithmic) amplifier of a form intended for use in connection with photometric measurements. The output signal from the photomultiplier 28 is fed to the board A where it is amplified, detected (transformed from AC into DC), and passed through the logarithmic amplifier. The board A also carries the circuit which provides for zero-setting during the kinetic analysis, and which subtracts a reference level corresponding to the container and blank absorption from the photometer reading to effect zero setting for colorimetric readings.

The circuit board B forms a concentration convertor which allows the signal fed from the board A, which represents linearized absorption of light through the liquid sample, to be converted to a liquid concentration signal with a multiplying factor K from 0.01 to 9.99. This factor K is adjustable by a digital-type control C5. A control C4 sets the output operational mode of the analyser by selecting either the linearized absorption signal fed from the board A or the concentration signal produced by the board B to be passed to the next stage of the analyser on the board C.

The circuitry on board C forms a digital voltmeter which converts the analogue signal fed to the board C from the control C4 into a digital one.

The digitised signal is fed to print-out control logic L and to a luminous display unit arranged on the board D. The display unit is preferably of the segment type and is arranged to be read through a window 58 in the panel 14 (see FIG. 5). A comparator, voltage adjuster and memory are arranged on the board G and effect automatic zero-setting operations of the analyser in response to enabling signals from programming circuitry on the board F. The circuitry of the board G acts as a Sample and Hold circuit and governs the sensitivity of the photomultiplier 28 (as can be seen from FIG. 8) so that it is possible to obtain a zero reading on the display unit when the container is in its outer, extracted position, this 'Automatic Zero' as it is commonly called is the electric or instrumental zero of the photometer.

The board F carries the programming circuitry controlling the operation and print-out of the analyser and includes timing circuits controlling timing of the analysis cycle, a circuit controlling the omission of the zero-setting "on the blank" procedure when the analyser is set to carry out kinetic analysis, and a thermostatic control device for regulating the temperature of the container 24. Thus board F in conjunction with controls C7 and C8, provides a programmed, automatic control of the analysis cycle.

Board H carries stabilizing circuits for supplying stabilized voltages to various parts of the analyser as required. Power is fed to the board H from the transformers 52 which have multiple outputs.

The board E carries a counter for numbering the printed analysis readings, the counter being indexed from the programming circuitry on board F. The print-out unit L can, for example, have six print columns; the first two columns are for numbering the readings of the sample being analysed (the number associated with a particular sample being reprinted for each reading made during a series of readings on that one sample that is, during kinetic analysis). The numbering is automatic from 1 to 99 and is repetitive.

The controls of the apparatus and their functions will now be listed.

C1 is a selection control for the interferential filters and is arranged to rotate the disc 20 into a selected one of, for example, 12 angular positions to thereby select a particular filter.

C2 is the main electric supply ON/OFF switch.

C3 is a temperature-setting control of the thermostatic control device of the card F and enables the temperature at which the container 24 is held to be preselected.

C4 is a selector switch control for selecting between readings of optical density or concentration.

C5 is a digital-type control for setting the factor K within the range 0.01 to 9.99.

C6 is arranged to set the automatic zero setting point of ± 400 units in D.O.; and it serves to set up the analyser to the reference solution (for instance, water or mixture of reagents). After the container with the 'blank' or other reference solution is moved back into its inner position, it is possible, by using the control C6 to adjust a reference level, to subtract or add up to 400 units in D.O., so as to bring the display unit reading to zero (obviously provided that said blank does not overcome the 400 units in D.O.).

C7 enables selection of a delay time before print-out of the first analysis reading (for example, selectable delay times of 3, 10, 30 and 60 seconds), a delay being necessary to ensure that steady state conditions exist in the liquid sample before readings are taken.

The control C8 sets the number of the readings (for example, selectably 1, 2, 4 and 6) to be taken in a minute, at uniform time intervals.

C9 permits an additional analysis and print-out cycle to be implemented for any one particular sample under analysis.

C10 is an optional control which enables an operator to actuate the print-out programming circuitry to advance the print-out paper by one line; this advance is in addition to the automatic feed after each print-out.

The control C11 is a zero-setting for the print-out unit counter which progressively numbers the analyses.

The control C12 (FIG. 8) comprises the micro-switch 38 (FIG. 7) which, as already stated, is actuated each time the slide member 30 is slid outwards to enable a liquid sample to be introduced into the container 24. Actuation of the micro-switch 38 sends an enabling signal to circuitry on the board F to initiate automatic zero setting on the blank. Return of the container unit into its inner, measurement, position, causes the microswitch 38 to initiate the taking of sample analysis readings after the delay time set by the control C7.

During kinetic analysis, the programming circuitry enables a delay time for example of 3, 10, 30 or 60 seconds to be set between re-insertion of the container unit and the start of the analysis printing cycle. After this delay, zero setting on the initial absorption value takes place followed by automatic print-out of subsequent readings, the number of which in any 1 minute can be set to be, for example two, four or six at intervals of 30, 15 or 10 seconds respectively. If a more detailed analysis is required, then the analysis cycle can be repeated by pressing a pushbutton forming the control C9.

I claim:
1. A photometric liquid analyzer, comprising:
   a photometric unit having
      a light source,
      a rotary modulator arranged to modulate light from the light source,
      at least one interferential filter through which the modulated light is arranged to pass,
      a photomultiplier,
      an optical system arranged to focus the said light, after passage through the filter, onto the photomultiplier, and
      a liquid-sample container unit movable into and out of an analysis position;
   the liquid-sample container unit comprising
      a container lying in the path of light passing from the optical system to the photomultiplier when the container unit is in the analysis position,
      a cycle-start automatic control arranged to initiate analysis of a liquid sample in the container upon the return of the container unit into the analysis position,
      a suction-emptying system for removing analysed liquid from the container, and
      a thermostatic control system for regulating the temperature of liquid in the container;
   electronic circuit means connected to the output of the photomultiplier to receive and process signals fed therefrom caused by light which has passed through the liquid sample in the container; and
   a print-out unit connected to the circuit means to receive the processed signals and to print out analysis readings in dependence thereon.

2. An analyser according to claim 1, comprising a plurality of interferential filters from which the said filter through which the malulated light is arranged to pass, is selectable.

3. An analyser according to claim 1, comprising
   a lower housing containing the said photometric unit, and
   an upper housing containing the said print-out unit, the upper housing being mounted on and inclined forwardly and upwardly with respect to the lower housing.

4. An analyser according to claim 3, in which each said housing comprises
   a shell,
   a removable lid fitting on the shell,
   side matching rules, and
   a front control panel.

5. An analyser according to claim 3, in which the lower housing has
   an upper surface with an opening defined therein, the analyser further comprising
   an intermediate housing arranged between the upper and lower housing and having an open rear, the intermediate housing communicating with the lower housing through the said opening in the upper surface of the lower housing,
   an intake fan disposed within the said opening whereby to remove air from the lower housing and expel it out of the open rear of the intermediate housing to ventilate the lower housing, and
   air intake means located in the lower housing to facilitate cooling of the lower housing by air flow therethrough.

6. An analyser according to claim 1, which the liquid-sample container unit further comprises
   a slide member carrying the said container and having a shallow groove and a deep groove defined therein,
   guide means for guiding movement of the slide between a first position in which the liquid-sample container unit is in the said analysis position, and a second, extracted, position, and
   a tappet engaging the slide member whereby to define the said first and second positions thereof in cooperation with the deep and shallow grooves respectively, engagement of the tappet in the deep groove allowing movement of the tappet to actuate the said cycle-start automatic control.

7. An analyser according to claim 6, in which the slide member carries a body which contains the said container, the body having a funnel through which liquid can be introduced into the container, and a fluid circuit of the said thermostatic control system, the thermostatic control system further comprising a thermostat and heating means controlled by the thermostat.

* * * * *